United States Patent [19]

Metais et al.

[11] Patent Number: 4,983,162
[45] Date of Patent: Jan. 8, 1991

[54] IMPLANTABLE DEVICE FOR ACCESS TO THE BLOOD CIRCULATORY SYSTEM

[75] Inventors: Joël Metais, Monts-sur-Guesnes; Gérard Lehmann, Avanton, both of France

[73] Assignee: LG Medical, Chasseneuil, France

[21] Appl. No.: 276,604

[22] Filed: Nov. 28, 1988

[30] Foreign Application Priority Data

Nov. 23, 1987 [FR] France ................................ 87 16195

[51] Int. Cl.$^5$ ............................................. A61M 39/00
[52] U.S. Cl. ........................................ 604/43; 604/175; 251/346; 137/614.17
[58] Field of Search ................. 604/175, 43, 181, 183, 604/175, 891.1; 606/153, 155, 156; 137/614.16, 614.17; 251/319, 341, 346, 347, 351

[56] References Cited

U.S. PATENT DOCUMENTS

| | | | |
|---|---|---|---|
| 4,294,285 | 10/1981 | Joslyn | 137/614.16 |
| 4,405,320 | 9/1983 | Cracauer et al. | 604/175 |
| 4,496,350 | 1/1985 | Cosentino | 604/175 |
| 4,654,033 | 3/1987 | Lapeyre et al. | 604/175 |
| 4,804,369 | 2/1989 | Lapeyre et al. | 604/43 |

FOREIGN PATENT DOCUMENTS 0007509 12/1987 World Int. Prop. O. ............ 604/27

Primary Examiner—Randall L. Green
Assistant Examiner—David H. Willse
Attorney, Agent, or Firm—Pollock, VandeSande & Priddy

[57] ABSTRACT

To provide access to the circulatory system, and to allow withdrawal and return of blood, of a living body, a T shaped implantable device includes a bar having outlet ends connected to the circulatory system, and a shaft having an end for forming an access well connectable to an external exchange system. The device can be connected, or disconnected, to the external exchange system by means of a rotary plug which is in the shape of a substantially cylindrical, circular disk whose outer diameter corresponds substantially to the inside diameter of the access well. The rotary plug operates in conjunction with a complementary component in the access well to ensure that the disk bears with pressure on the bottom of the access well, such that the closure of the well is leakproof.

6 Claims, 7 Drawing Sheets

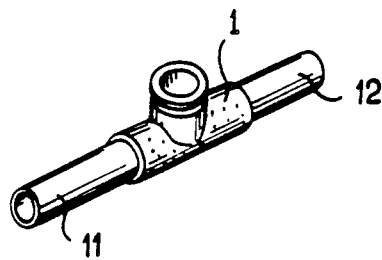
FIG_1
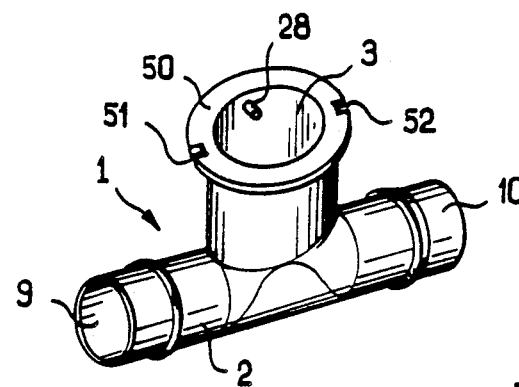
FIG_2
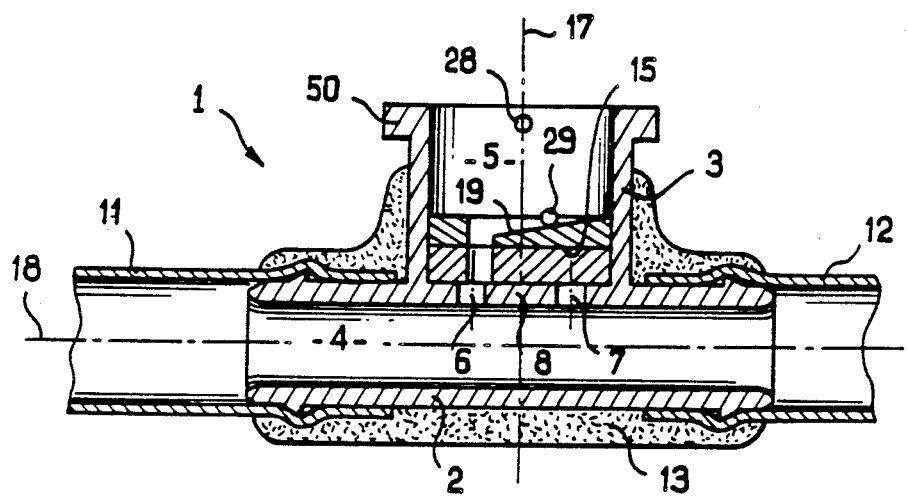
FIG_3

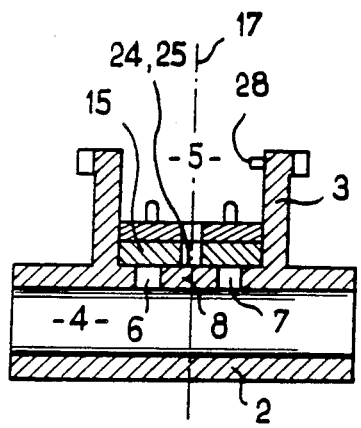
FIG_9
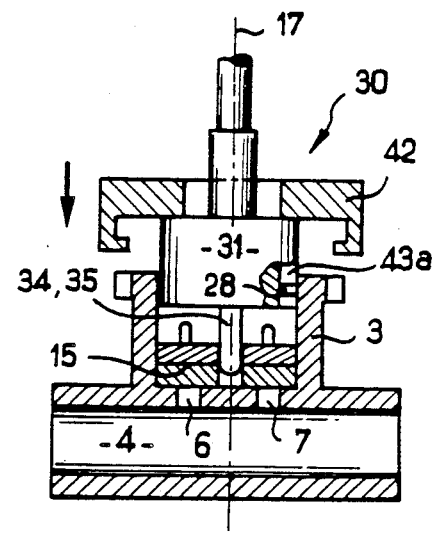
FIG_10
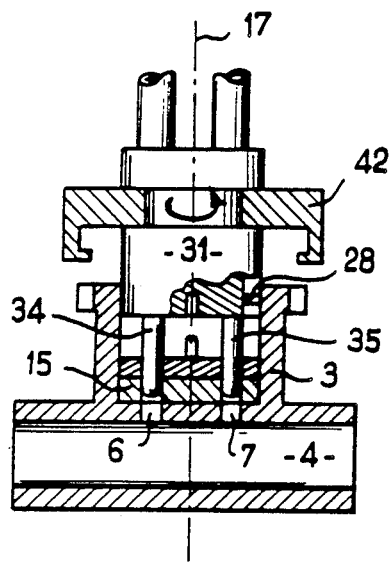
FIG_11
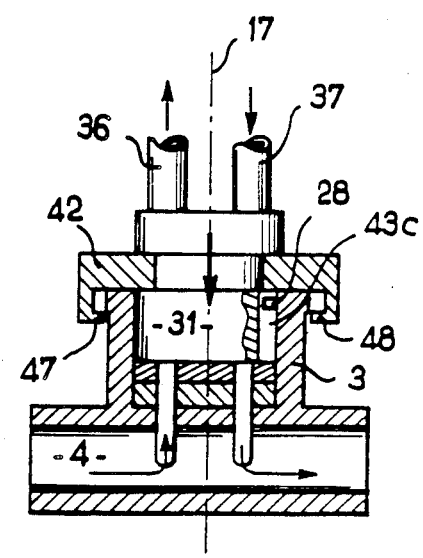
FIG_12

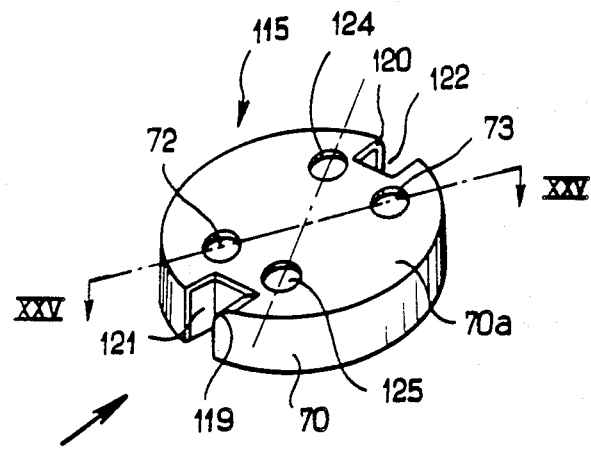
FIG_23
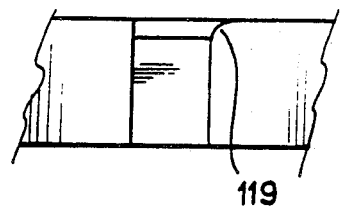
FIG_24
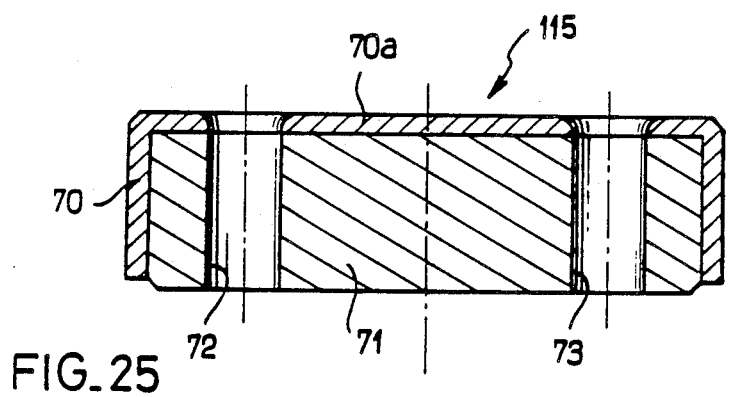
FIG_25
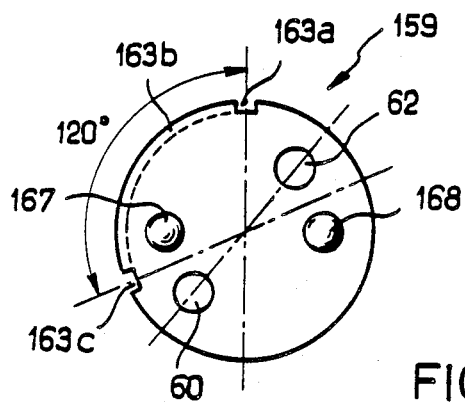
FIG_26

IMPLANTABLE DEVICE FOR ACCESS TO THE BLOOD CIRCULATORY SYSTEM

FIELD OF THE INVENTION

The invention relates to an implantable device, for access to the blood circulatory system, of the type comprising essentially a tee piece (T) in which the outlet ends of the bar or branch are connected to veins, arteries or vascular prostheses, and in which the end of the shaft forming the access well can be connected to any external exchange system, for example for dialysis of the blood of a patient, and in which the connection/disconnection with respect to the exterior is achieved by means of a component mounted in the said well and forming a rotary plug comprising two orifices which, depending on the position of rotation of the rotary plug, are in communication with or not in communication with the internal volume of the branch of the tee and which, on the other hand, can be connected to the inlet and to the outlet of the said external system.,

DISCUSSION OF THE PRIOR ART

Such devices are known and are described for example in U.S. Pat. No. 4,108,173. These devices have great advantages for the patient in terms of use and comfort, avoiding, for each operation on the circulatory system, the need to find a possible site at which to carry out the new operation with, in particular in the case of dialysis, needles of particularly large diameter. But the known devices are of very complex design, are consequently extremely expensive and present various difficulties in terms of use, especially in the event of servicing of the constituent parts or necessary replacement of a component subject to wear.

BRIEF DESCRIPTION OF THE INVENTION

The device according to the invention is characterized in relation to the devices described hereinabove of the general type in that the rotary plug is in the form of a substantially cylindrical, circular disk whose outer diameter corresponds substantially to the inside diameter of the well comprising means cooperating with complementary means of the said well in order to ensure, at least in the disconnection position of the device, that the disk bears with pressure on the bottom of the well and that the closure of the well is leakproof. Advantageously, and according to an embodiment which is simple to implement, the complementary means in question consist of ramps formed on the disk and cooperating with spurs formed on the inner wall of the well.

According to an essential characteristic of the invention, the device additionally comprises a connecting device for joining to the external system that includes a stopper which can engage in a leakproof manner in the well. And two hollow spindles capable of passing through the abovementioned orifices in a leakproof manner formed in the rotary plug. This connecting piece additionally comprises means for guiding and orientation in the well, such that at least one groove is formed in its side wall cooperating with a finger provided on the wall of the well to imparting a movement of introduction of the connecting piece. The movement comprises at least a first insertion movement until the spindles penetrate into the orifices of the rotary plug when in the closed position, then a movement of rotation to bring the rotary plug into the open position, then a new rectilinear insertion movement until the spindles penetrate to the desired level into the internal volume of the branch of the tee, the withdrawal movements of the connecting piece being the reverse of those of introduction and at the same time entailing the necessity of positioning the rotary plug in the closed position before withdrawal of the connecting piece.

It appears that in this way the operation, that is to say the act of connection and disconnection with regard to the external system of, for example, dialysis or perfusion, is performed very simply, without any possibility of maneuvering error or any particular difficulty.

According to a very advantageous characteristic of the invention, the device additionally comprises an extractor device comprising, like the connecting piece, a stopper which can engage in a leakproof manner in the well, which stopper comprises two orifices for the passage of spindles capable of passing through the above-mentioned orifices formed in the rotary plug. This extractor additionally comprises means for guiding and orientation in the well such that at least one groove formed in its side wall cooperates with a finger provided in the wall of the well to impart a movement of introduction of the extractor. The movement comprises at least a first insertion movement until the spindles penetrate into the orifices of the rotary plug when in the closed position, then a movement of rotation to bring the rotary plug into the open position. In this position the spindles can be inserted through the orifices of the wall at the bottom of the well, which they seal; and then, with the spindles remaining in place, the extractor can be withdrawn in an extraction movement parallel to the axis of the well, taking with it the rotary plug by virtue of the provision of at least one groove parallel to the axis of the well and in which is engaged the said finger in this position of rotation of the extractor. It will be understood that, in this way, it is possible to change the rotary plug in a simple manner, which plug constitutes the only wearing piece in the system, and this without any loss of blood.

BRIEF DESCRIPTION OF THE DRAWINGS

The invention and its implementation will appear more clearly from the following description, made by way of illustration, of exemplary embodiments.

In these drawings:

FIG. 1 shows diagrammatically and in perspective the tee piece connected to two vascular prostheses;

FIG. 2 shows on a larger scale, in an external perspective view, the tee piece alone;

FIG. 3 shows in section, in the center plane of the tee containing the axis of the well and the axis of the branch, the tee connected to the vascular prostheses, and in the well of which the rotary plug is placed in the closed position;

FIGS. 9, 10, 11 and 12 are diagrams illustrating the positioning and introduction of the connecting piece on the device;

FIG. 23 shows in perspective view the modified rotary plug of FIGS. 20 to 22;

FIG. 24 shows a detail in accordance with the arrow XXIV in FIG. 23;

FIG. 25 is a section on a larger scale made in the plane XXV—XXV of FIG. 23;

FIG. 26 shows an end view of the modified extractor which can be used with the rotary plug of FIGS. 23 to 25.

DETAILED DISCUSSION OF THE INVENTION

Figure 4:
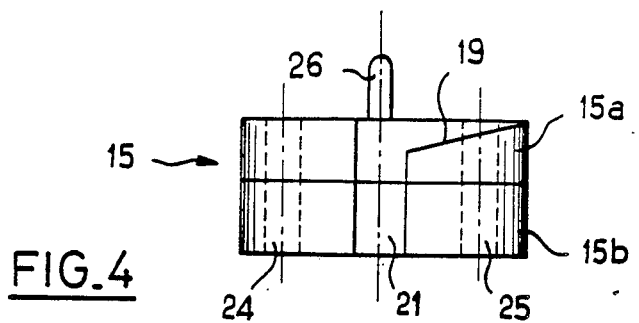
FIG. 4 shows on a larger scale, seen from the side, the rotary plug.

Reference will be made first of all to FIGS. 1 to 3 in the drawings.

Figure 19:
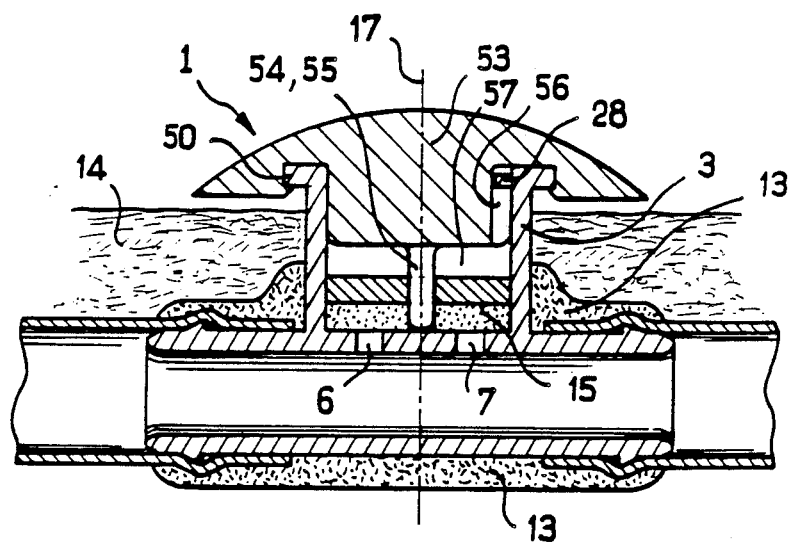
FIG. 19 is a cut-away view showing the device of the invention with its blocking stopper in position.

The implantable device for access to the blood circulatory system of a patient comprises essentially a tee element 1 comprising essentially a branch 2 forming the bar of the tee communicating with a well 3 forming the shaft of the tee. As can be seen more clearly from FIG. 3, the communication between the internal volume 4 of the branch 2 and the internal volume 5 of the well 3 is made by means of two orifices 6, 7 made through a wall 8 separating the volumes 4 and 5. At its ends 9 and 10 the branch 2 is, on the other hand, preferably connected to vascular prostheses 11, 12 previously arranged as is known. A compatible covering, for example Dacron velvet (trade name) or other biocompatible material, covers the part of the device implanted under the skin, as designated by 13. Reference may also be made to FIG. 19 showing the device 1 implanted in position under the skin, designated 14, of a patient.

Returning to FIG. 3, this figure also shows the rotary plug 15 in the blocking position in which the passages 6 and 7 are sealed by this rotary plug.

Figure 5:
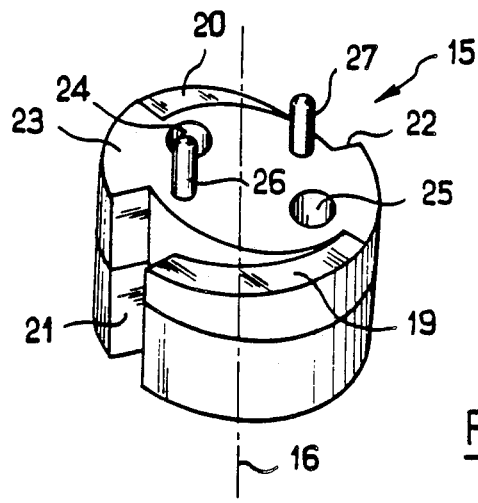
FIG. 5 shows the same rotary plug in perspective view.

The functioning and action of the rotary plug 15 will be more easily understood by referring to FIGS. 3, 4 and 5.

According to the exemplary embodiment illustrated, the rotary plug 15 is in a general fashion symmetrical about its vertical axis 16. In its position of introduction in the well 3, the axis 16 of the rotary plug 15 corresponds to the axis 17 of the well, which is perpendicular to the axis 18 of the branch 2.

On its upper face the rotary plug 15 comprises two ramps 19, 20, each beginning in a cut 21, 22, parallel to the axis 16 and ending level with the free outer face (the upper face as shown in the drawings) 23 of the rotary plug.

Two orifices 24, 25 are also made in the rotary plug which are substantially symmetrical and which pass fully through the rotary plug. It will be noted immediately, and we will come back to this later, that, in the use or connection position of the device, the orifices 24, 25 of the rotary plug are in line and communicate with the orifices 6, 7 of the bottom wall 8 of the well, these orifices 6, 7, 24, 25 preferably being circular and cylindrical, and of the same diameter.

In the exemplary embodiment illustrated, the rotary plug 15 is made up of two parts, namely a bearing disk 15a and a washer 15b. The bearing disk can be made of different materials such as, in particular, titanium or a hard plastic material of appropriate quality such as, for example, polyethylene or polypropylene. The washer 15b can be a silicone washer which can be stuck or molded onto the piece 15a. In this case the piece thus produced has, overall, a certain elasticity permitting good leakproofness by compression when the rotary plug is closed, as will be explained hereinafter. But in other embodiments the pieces 15a and 15b can be made integral and of a single material such as, graphite, ceramic material, and polytetrafluoroethylene (PTFE) This single piece is thus rigid, and the leakproofness upon closure is achieved simply by means of the perfect matching, one to the other, of the polished lower face of the rotary plug and the face opposite which forms the bottom of the well.

Finally, returning to FIGS. 4 and 5, two substantially cylindrical pins 26, 27 can be seen on the top of the rotary plug and projecting above the upper face 23. The role of these pins will emerge hereinafter.

Returning to FIG. 3 there can also be seen, projecting from the inner wall of the well 3 to the interior of the volume 5, respectively, a finger 28 for guiding and positioning the connecting piece and the extractor, as will emerge later, and one 29 of two spurs arranged in symmetry on the wall of the well and cooperating with the ramps 19, 20 of the rotary plug, as will be described hereinafter.

The device forming the connecting piece and part of the entire device according to the invention will now be described with reference to FIGS. 6 to 8. The connecting piece designated overall by 30 comprises essentially a stopper 31 which can engage in the well 3 preferably in a substantially leakproof manner. It can be made, for example, of a material such as polyethylene, and the material forming the well 3 and the branch 2 of the tee element can be, for example, titanium with a pyrolite covering, or graphite with a pyrolite covering, or else polytetrafluoroethylene (PTFE). In the inside of the stopper 31 of the connecting piece two orifices 32, 33 are found permitting the leakproof passage of two spindles 34, 35 which are, for example, of stainless steel of appropriate quality and will be connected to tubes 36, 37 for connection to the exterior, for example a dialysis machine (not shown).

The relative dimensioning and positioning of the spindles 34 and 35 obviously correspond to the relative dimensioning and positioning of the orifices 24, 25 of the rotary plug in which these spindles will be able to penetrate, and they will be able to pass through in a substantially leakproof manner.

At the lower end of the spindles 34, 35 can be seen the orifices 38, 39, slightly off-set in height, for the entry and the withdrawal of, for example, dialyzed blood during use of the device.

Figure 6:
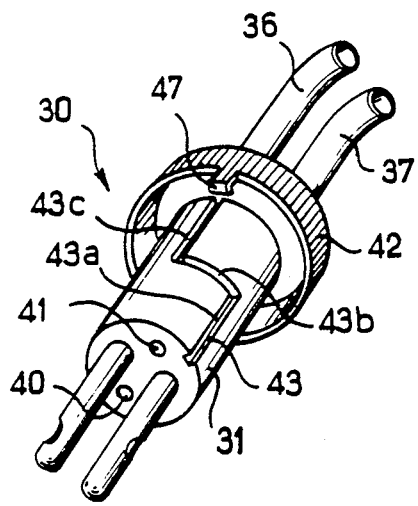
FIG. 6 shows in perspective view the assembly of the connecting piece with its locking collar.

On its lower face, as can be seen more clearly in FIG. 6, the stopper 31 of the connecting piece comprises two blind holes 40, 41 for receiving, with sufficient play, the pins 26, 27 of the rotary plug. In the upper part of the connecting piece can be seen the locking collar 42 which permits the advantageously leakproof blockage of the connecting piece on site during an operation, for example dialysis.

Finally, referring more particularly to FIG. 6, there can be seen, on the side wall of the stopper 31 of the connecting piece, a recessed groove 43 successively comprising three sections 43a, 43b and 43c defining a step, the first section 43a being directed parallel to the longitudinal axis 44 of the connecting piece, as is the final section 43c, while the middle section 43b in a plane perpendicular to the axis 44 defines a quarter-turn on the outer wall of the stopper 31.

Figure 7:
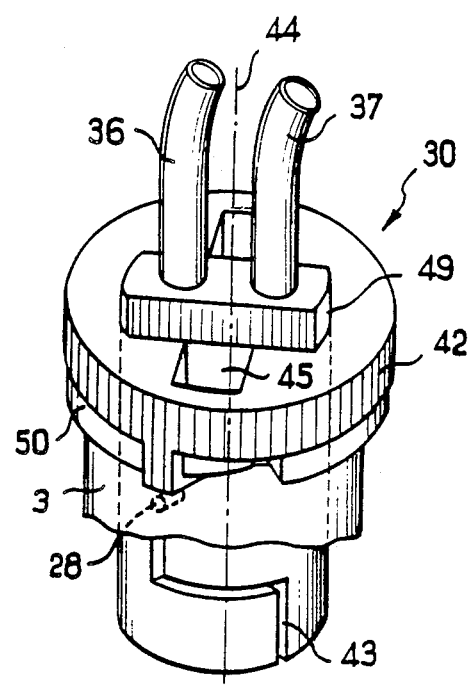
FIG. 7 shows the same connecting piece on a larger scale, and seen from another angle, with parts omitted.
Figure 8:
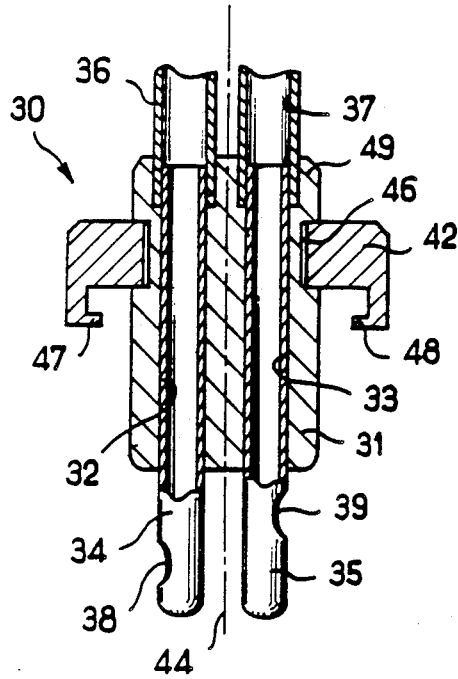
FIG. 8 shows in longitudinal section the connecting piece with its locking collar.

In FIGS. 7 and 8 there can also be seen the assembly of the blocking collar 42 on the stopper 31 permitting the rotation in a channel 46 formed towards the upper part of the stopper 31, as well as the provision of a recess 45 in the collar 42 permitting, in a relative position of rotation of the collar 42 relative to the stopper 31, the positioning of the collar 42 in its guide channel 46, and this by virtue of the conjugate form of the upper shoulder 49 of the stopper 31. FIGS. 6 to 8 also show two fingers 47, 48 forming returns which can engage, after positioning of the connecting piece in the well 3, under the neck 50 of the well.

The functioning of the device will now be described with reference more particularly to FIGS. 9 to 12.

As regards FIG. 9 first of all, it has been assumed that the device is in place, the rotary plug 15 being in the closed position. In this position the orifices 24, 25 of the rotary plug, which are visible one behind the other in the axis 17 of the well, do not communicate with the orifices 6, 7 in the bottom wall 8 of the well. Thus, the volumes 5 and 4 of the well and of the tee branch are not in communication. On the contrary, they are isolated in a leakproof manner by virtue of the rotary plug bearing with pressure on the bottom of the well. As will emerge more clearly from a comparison of FIGS. 3 and 5, this is achieved because, in this rotation position of the rotary plug 15, the spurs 29 are engaged under the ramps 19, 20 of the rotary plug in their high section and thus, by means of this ramp effect, press the flat bottom of the rotary plug 15 firmly against the flat bottom opposite of the well.

Referring now to FIG. 10, this illustrates the phase in which the connecting piece 30 is brought into position over the well. More precisely, the stopper 31 of the connecting piece is introduced into the wall of the well. But this introduction can only be effected in the angular position in which the groove 43 (FIG. 6), and more precisely the section 43a of this groove, is opposite the finger 28 for guiding the connecting piece. This position corresponds very precisely to the position in which the spindles 34, 35 (visible one behind the other in the axis 17 of the well) are in alignment with the orifices 24, 25 of the rotary plug, into which orifices the said spindles can engage. The length of the section 43a is calculated such that, when the finger 28 comes to the end of this groove, penetrating inside the section 43b, the spindles 34, 35 have substantially passed through the entire thickness of the rotary plug 15.

At this stage the insertion of the spindles and of the stopper 31 into the well 3 may be continued only if, first, the connecting piece is rotated a quarter-turn as indicated in FIG. 11. In such a movement the finger 28 describes the section 43b of the groove 43. At the same time the spindles 34, 35, which have penetrated into the orifices 24, 25 of the rotary plug, impart a quarter-turn to the latter. The effect of this rotation is to:

release the action of the pressure of the spurs 29 on the ramps 19, 20, to bring the orifices 24, 25 of the rotary plug opposite the orifices 6, 7 for communication in the well bottom.

However, it should be noted that the orifices 24, 25 are then in fact sealed in a leakproof manner by the spindles 34, 35.

In this position it thus becomes possible, as illustrated in FIG. 12, to insert the stopper 31 further into the well 3, the finger 28 having in fact come into position opposite the section 43c of the groove 43. In such an insertion movement the spindles then pass through the orifices 6, 7 at the well bottom and penetrate into the volume 4, producing the connection of the external system to the vascular prostheses 11, 12 (see FIG. 3) in connection with the volume 4. The dialysis system can then function, the tubes 36 and 37 being in communication with the vascular prostheses. In this position the locking collar 42 is then lowered under the neck 50 of the well, by pushing the return locking fingers, 47, 48 into the notches 51, 52 made for this purpose in the neck (see FIG. 2) and then by turning the collar under the neck. The connecting piece is thus locked in position on site.

It is clear that the operations for disconnection are carried out in a manner which is strictly the reverse of those operations for connection.

In brief, the collar 42 will be unlocked first, and it will then be possible to withdraw the connecting piece partially as far as the blocking of the finger 28 at the end of the rectilinear section 43c of the groove 43; after this a quarter turn is made in the direction opposite to that described in FIG. 11, the finger 28 describing in reverse direction the section 43b of the groove 43, and the spindles 34, 35 at the same time driving the rotary plug 15 in positive locking in the well by virtue of the engagement of the ramps 19, 20 of the rotary plug under the locking spurs 29. When the complete quarter turn has been carried out, the connecting piece can then be withdrawn, the rectilinear groove section 43a at that moment being opposite the finger 28.

Referring to FIG. 19 it can be seen that at this point it is possible to lock the device in this state by simply pressing over the neck 50 of the well 3 a stopper 53 made of plastic material of appropriate quality, for example injected polyethylene. This stopper 53 comprises two spindles 54, 55 which appear in FIG. 19 one behind the other in axis 17 of the well 3. These spindles have a position which corresponds to that of the orifices 24, 25 of the rotary plug 15 in this position of closure. The satisfactory positioning of the stopper 53 is assured by a groove 56 which must be engaged over the finger 28 for positioning the connecting piece as has been described hereinabove. In this way a safeguard is achieved against any ill-timed unlocking of the rotary plug 15. It will be noted that, in the space under the stopper 53 and above the rotary plug 15, the space being designated 57, it will be possible to introduce an appropriate disinfectant.

By referring now to FIGS. 13 to 18 a description will be given of a complementary device forming an extractor as well as its functioning which permits, if required for maintenance of the device, replacement of the rotary plug 15.

Figure 13:
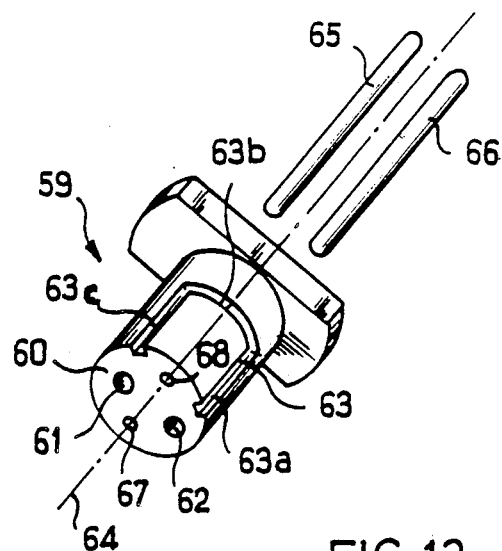
FIG. 13 is a perspective view showing an extractor used according to the invention.

Referring to FIG. 13, the extractor, designated as a whole by 59, is made up essentially of a stopper 60 pierced by two orifices 61, 62. The stopper 60 can have dimensions entirely similar to those of the stopper 31 of the connecting piece, and the orifices 61, 62 are also advantageously similar in dimension and positioning to the orifices 32, 33 of the connecting piece.

On the side wall of the extractor there is a groove 63 of general U shape having a first section 63a starting at the base of the stopper 60 and extending over a certain length parallel to the axis 64 of the stopper, a curved quarter circle section 63b situated in a plane perpendicular to the axis 64, then a third section 63c parallel to the section 63a and returning to the base of the stopper 60.

FIG. 13 also shows two spindles which can be simple solid steel rods 65, 66 capable of engaging in and substantially sealing the orifices 61, 62 of the stopper. These spindles 65, 66 have substantially the same outside diameter as the spindles 34, 35 described previously in relation to the connecting piece 30.

FIG. 13 also shows two blind holes 67, 68 offset by 90° relative to the orifices 61, 62, the importance of these blind holes being explained hereinafter.

The functioning of the extractor will be described with reference to FIGS. 14 to 18.

Figure 14:
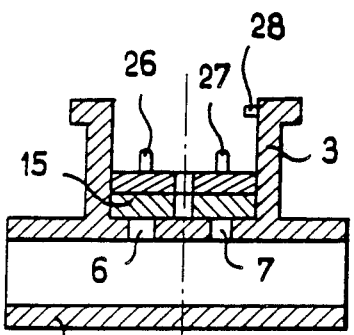
FIGS. 14 to 18 are diagrams illustrating the use of the extractor.

FIG. 14, like FIG. 9, shows the device with the protecting stopper 53 removed and the rotary plug 15 in the closed position.

Figure 15:
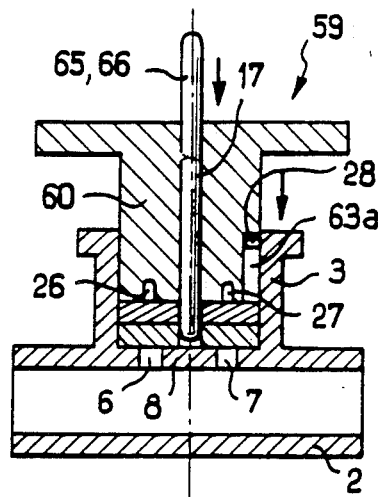

The extractor 59 is then positioned in the well, as illustrated in FIG. 15, by inserting the stopper 60 in a leakproof manner into the well 3. This operation is carried out by bringing the finger 28 into the groove 63a. In this relative angular position the spindles 65, 66, which have been inserted through the stopper 60, are aligned one behind the other in the axis 17 of the well and also come into alignment with the orifices 24, 25 of the rotary plug 15 in the closed position which it occupies. They can be inserted until they are substantially against the bottom wall 8 of the well. As regards the pins 26, 27 projecting from the upper face 23 of the rotary plug 15, these engage in the previously mentioned blind holes 67, 68 of the stopper 60. The pins advantageously have a substantially cylindrical circular shape, while the blind holes 67, 68 of substantially equivalent diameter are slightly tapered with a cross-section narrowing from the outlet of the hole to the base. In this way, when the extractor is applied over the rotary plug, the pins 26, 27 lock elastically in the blind holes 67, 68.

Figure 16:
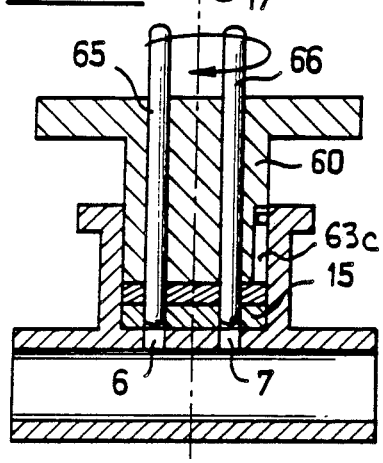

As illustrated in FIG. 16, the stopper 60 is then given a quarter turn, the branches 65, 66 turning simultaneously and moving the rotary plug 15 whose orifices come into position opposite the orifices 6, 7 formed in the bottom of the well.

Figure 17:
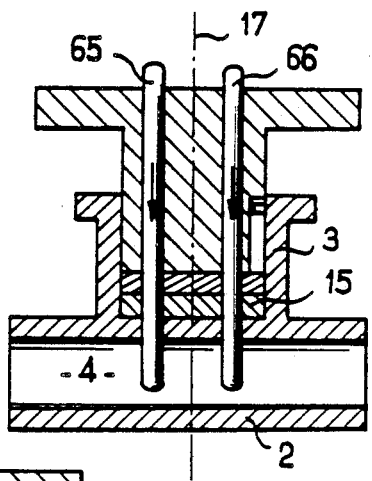

As illustrated in FIG. 17 the spindles 65, 66 are then inserted further, allowing them to penetrate through the orifices 6 and 7 which they seal so as to separate, in a leakproof manner, the volume 4 of the branch 2 with respect to the exterior.

Figure 18:
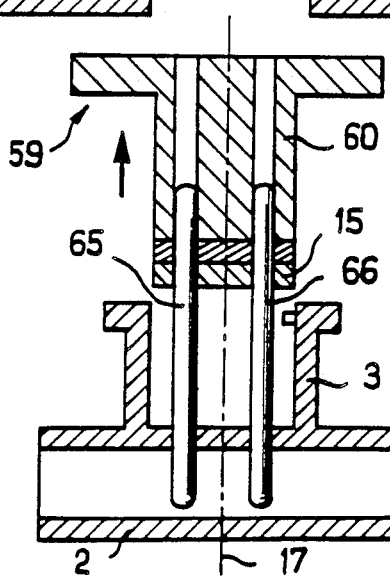

As illustrated in FIG. 18, it then only remains to withdraw the extractor 59 by lifting it parallel to the axis 17 of the well, allowing it to slide on the spindles 65, 66 which remain in place. In this movement the rotary plug 15, locked by the pins 26, 27 wedged in the tapered holes 67, 68 of the extractor, remains firmly attached to the latter.

The positioning of a new replacement rotary plug is carried out by operating in exactly the opposite manner to that which has just been described with reference to FIGS. 14 to 18, and it can be summarized as follows:
positioning of a new rotary plug 15 on an extractor,
introduction of the extractor and the rotary plug over the spindles 65, 66,
partial withdrawal of the spindles in such a way that they disengage the orifices 6 and 7,
rotation by 90° of the extractor, with simultaneous closure of the rotary plug at the bottom of the well,
withdrawal of the extractor.

From the preceding description it emerges that the device of the invention is of particularly simple production and use.

According to the variant illustrated in FIGS. 20 to 26, the rotary plug 115 exhibits some modifications compared to the rotary plug 15 used and illustrated in the preceding figures.

It is made up essentially of a metal dish 70, advantageously of titanium, in which there is accommodated and maintained, for example by slight compression, crimping or overmolding, a washer 71 of biocompatible elastomeric material, such as a silicone, of suitable plastic material etc. The washer 71 protrudes slightly below the skirt of the dish 70, as emerges more clearly from FIG. 25.

The rotary plug comprises two orifices 124, 125, which correspond to the orifices 24, 25 of the embodiment previously described, and also two other orifices 72, 73 which are of substantially equivalent diameter and whose use will emerge hereinafter.

As emerges more clearly from FIG. 24, the two cuts 121, 122 of the rotary plug, which are equivalent to the cuts 21, 22 of the previously described embodiment, have, on one side, a rounded part 119, 120 whose function is substantially equivalent to that of the ramps 19, 20 of the preceding embodiment, as will emerge from the following description of the functioning.

By referring to FIG. 25 it will also be seen that, facing the orifices such as 72, 73 of the rotary plug, a certain rounding and enlarging has been carried out in the upper wall 70a of the dish 70 in order to facilitate the introduction of the spindles through the rotary plug.

The use of the device thus modified will be briefly described.

Figure 20:
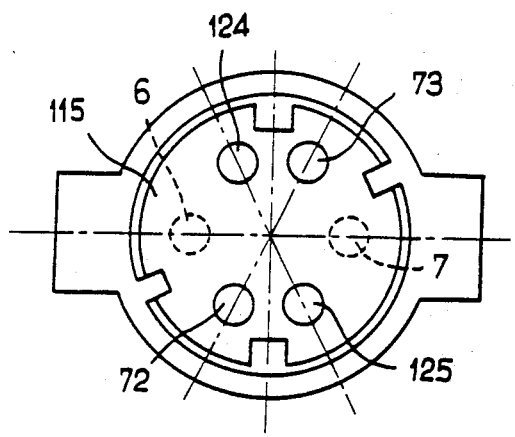
FIGS. 20, 21, 22 show diagrammatically, and in a plan view, the variant of a rotary plug occupying three different positions of rotation in the well.

FIG. 20 illustrates the position into which it will be possible to place the connecting piece in order to perform the dialysis, as has been described previously, in particular with reference to FIGS. 10 to 12.

Figure 21:
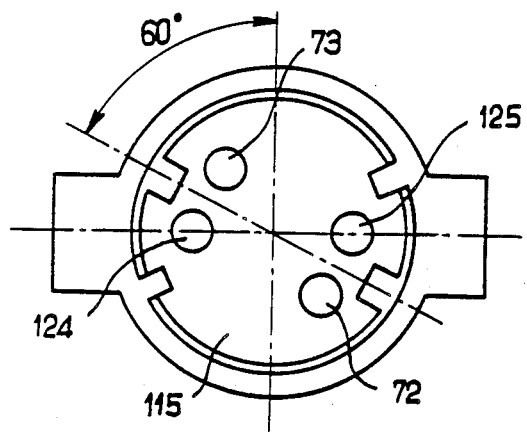

In a manner entirely similar to that described in the preceding embodiment the connecting piece is brought into the correct position, then the two spindles 34, 35 of the connecting piece are introduced into the corresponding orifices 124, 125 of the rotary plug, and then the system is subjected to a rotation of 60° as indicated in FIG. 21 (a rotation which was 45° in the previously described embodiment). After rotation of 60° the orifices 124, 125 of the rotary plug have come into position opposite the orifices 6, 7 respectively of the well bottom, and the spindles of the connecting piece can be inserted to the level suitable for dialysis.

Because of the modification to the design of the rotary plug it moreover appears that, from the start of the rotation from the introduction position illustrated in FIG. 20, the spurs 29 (FIG. 3) pass, by means of the rounded parts 119, 120, above the upper plane of the dish 70 by compressing the elastomeric washer 71, and thus ensuring a perfect leakproofness upon closure of the orifices 6, 7 of the well bottom against the lower elastomeric face of the composite rotary plug 115. This pressure is maintained for any angular position of the rotary plug other than the initial introduction position shown in FIG. 20. A perfect leakproofness of the system is thus ensured in all operational positions.

Figure 22:
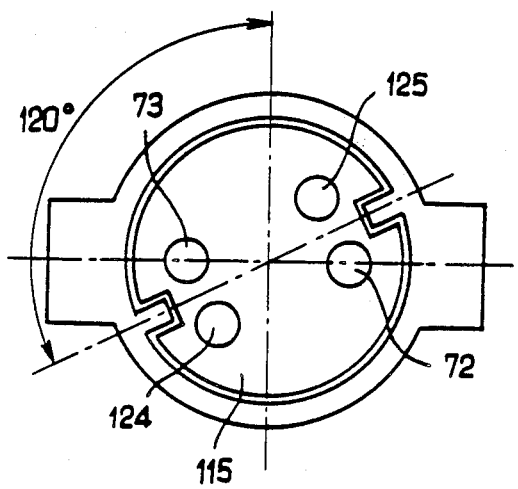

FIGS. 22 and 26 illustrate the position permitting a change of the rotary plug by virtue of the use of an extractor. In the variant thus shown the extractor tool 159 is modified slightly compared to the tool 59 illustrated in FIG. 13, essentially in that it comprises, instead of the two blind holes 67, 68 in FIG. 13, two pins in relief 167, 168. Likewise, the circular groove 63b, which made a quarter turn in the embodiment in FIG. 13, here runs through an angle of 120° between the rectilinear inlet groove 163a and the rectilinear outlet groove 163c, these two grooves being parallel to the axis of the extractor as in the embodiment in FIG. 13.

The modification in the functioning will now be described.

In order to effect the change of a rotary plug, the extractor is brought into position as previously described in relation to FIG. 13, the correct orientation being ensured by the introduction of the positioning finger 28 into the inlet groove 163a of the extractor tool. In this position of rotation the pins 167, 168 position themselves in the orifices 124, 125 of the rotary plug 115. They advantageously have a diameter slightly greater than that of the orifices 124, 125, thus ensuring an elastic locking of the rotary plug 115 on the extractor tool when the pins 167, 168 have been correctly introduced into the orifices 124, 125 formed in the elastomeric material of the washer 71.

This operation complete, it is necessary to turn, about an angle of 120° as illustrated in FIG. 22, the extractor tool and the rotary plug together in order to bring the orifices 72, 73 into position opposite the orifices 7 and 6 respectively of the well bottom. In this position it is then possible to introduce the spindles 65, 66 into the extractor as previously described in particular in relation to FIG. 15 to 18, which spindles will seal the orifices 6 and 7 of the well bottom. The orifices 72, 73 advantageously have a diameter slightly greater than that of the spindles, for example having a diameter of the order of 2.10 mm when the spindles have a diameter of 2 mm, the same diameter of 2 mm being provided for the orifices 6 and 7 and for the orifices 124, 125. The clearance thus formed permits the easy removal of the rotary plug 115 which remains locked on the extractor by means of the pins 167, 168 introduced into the orifices 124, 125, the extraction being permitted by virtue of the fact that the positioning finger 28 has this time come into position at right angles to the rectilinear groove 163c.

We claim:

1. An implantable device for access to the blood circulatory system, having a tee piece comprising:
    a bar or branch outlet, the ends of which are connected to veins, arteries or vascular prostheses;
    a shaft having an end for forming an access well which can be connected to an external exchange system;
    wherein the connection/disconnection of said device with respect to said external exchange system is achieved by means of a rotary plug mounted in said well, said rotary plug having two orifices which, depending on the position of rotation of said rotary plug, are in communication with or not in communication with the internal volume of the branch of the tee piece and which, at the other end can be connected to an inlet and to an outlet of said external system;
    wherein said rotary plug is in the shape of a substantially cylindrical, circular disk whose outer diameter corresponds substantially to the inside diameter of said well, said rotary plug further including:
        means cooperating with complementary means of said well in order to ensure, at least in the disconnection position, that said disk bears with pressure on the bottom of said well and the closure of said well is leakproof;
    said complementary means having ramps formed on said plug cooperating with spurs formed on the inner wall of said well.

2. An implantable device, for access to the blood circulatory system, having a tee piece comprising:
    a bar or branch outlet, the ends of which are connected to veins, arteries or vascular prostheses;
    a shaft having an end for forming an access well which can be connected to an external exchange system;
    wherein the connection/disconnection of said device with respect to said external exchange system is achieved by means of a rotary plug mounted in said well, said rotary plug having two orifices which, depending on the position of rotation of said rotary plug, are in communication with or not in communication with the internal volume of the branch of the tee piece and which, on the other hand, can be connected to an inlet and to an outlet of said external system;
    wherein said rotary plug is in the shape of a substantially cylindrical, circular disk whose outer diameter corresponds substantially to the inside diameter of said well, said rotary plug further including:
        means cooperating with complementary means of said well in order to ensure, at least in the disconnection position, that said disk bears with pressure on the bottom of said well and the closure of said well is leakproof;
    a connecting piece for joining to said external system, said connecting piece further including:
        a stopper which can engage in said well;
        two hollow spindles, capable of passing through the orifices formed in said rotary plug, passing in a leakproof manner through said stopper;
    wherein said connecting piece further includes:
        means for guiding and aligning in said well having at least one groove formed in its side wall cooperating with a finger provided on the wall of said well;
    wherein said connecting piece is introduced into said tee piece by the steps of:
        inserting said connecting piece into said well until the spindles penetrate into the orifices of said rotary plug when in a closed position;
        rotating said rotary plug into an open position;
        rectilinearly inserting said connecting piece until the spindles penetrate to a desired level into the internal volume of the branch of the tee piece; and
    wherein said connecting piece is withdrawn from said device in accordance with steps in reverse of the steps used to introduce said connecting piece to said device, the positioning of said rotary plug being in the closed position before withdrawal of said connecting piece.

3. The device as claimed in claim 2, further comprising:
    a locking collar on the neck of said well to permit, by rotation of the collar, the locking in translation of said connecting piece in the collar on the well when said connecting piece is in position.

4. An implantable device, for access to the blood circulatory system, having a tee piece comprising:
    a bar or branch outlet, the ends of which are connected to veins, arteries or vascular prostheses;

a shaft having an end for forming an access well which can be connected to an external exchange system;

wherein the connection/disconnection of said device with respect to said external exchange system is achieved by means of a rotary plug mounted in said well, said rotary plug having two orifices which, depending on the position of rotation of said rotary plug, are in communication with or not in communication with the internal volume of the branch of the tee piece and which, on the other hand, can be connected to an inlet and to an outlet of said external system;

wherein said rotary plug is in the shape of a substantially cylindrical, circular disk whose outer diameter corresponds substantially to the inside diameter of said well, said rotary plug further including:

means cooperating with complementary means of said well in order to ensure, at least in the disconnection position, that said disk bears with pressure on the bottom of said well and the closure of said well is leakproof;

an extractor device having a stopper which can engage in said well, said stopper including two orifices for the passage of spindles capable of passing through the orifices formed in said rotary plug, wherein said extractor additionally includes:

means for guiding and aligning in said well including at least one groove formed in its side wall cooperating with a finger provided on the wall of said well;

wherein said extractor is introduced into said tee piece by the steps of:

inserting said stopper into said well until the spindles penetrate into the orifices of said rotary plug when in a closed position;

rotating said rotary plug into an open position, the spindles being inserted through the orifices of the well at the bottom of said well in this position;

then, with the spindles remaining in place, withdrawing said extractor by extracting the same in parallel to the longitudinal axis of said well, taking with it said rotary plug by virtue of at least one groove being provided parallel to the axis of said well and in which is engaged said finger.

5. The device as claimed in claim 4, wherein said rotary plug comprises on its outer face at least two pin means capable of forcibly engaging bores in said extractor.

6. The device as claimed in claim 4, wherein said rotary plug comprises four orifices arranged in diametrically opposite pairs, and corresponding in coincidence to the orifices at the bottom of said well for two different positions of rotation, one corresponding to a position for dialysis, the other corresponding to a position for changing said rotary plug, with corresponding passage of the spindles.

* * * * *

UNITED STATES PATENT AND TRADEMARK OFFICE
CERTIFICATE OF CORRECTION

PATENT NO. : 4,983,162
DATED : January 8, 1991
INVENTOR(S) : Joel Metais, et al.

It is certified that error appears in the above-identified patent and that said Letters Patent is hereby corrected as shown below:

Column 1, line 56, change "well. And two" to

--well, and two--.

Column 1, line 58, after "manner" insert --are--.

Column 1, line 62, change "imparting" to --impart--.

Column 9, line 30, change "FIG." to --FIGS.--.

Signed and Sealed this

Twelfth Day of May, 1992

Attest:

DOUGLAS B. COMER

*Attesting Officer*   *Acting Commissioner of Patents and Trademarks*